United States Patent
Iwata

(10) Patent No.: US 6,955,760 B2
(45) Date of Patent: Oct. 18, 2005

(54) LIQUID CHROMATOGRAPH

(75) Inventor: Yosuke Iwata, Kyoto (JP)

(73) Assignees: Shimadzu Corporation, Kyoto (JP); Eisai Co., Ltd., Tokyo (JP)

( * ) Notice: Subject to any disclaimer, the term of this patent is extended or adjusted under 35 U.S.C. 154(b) by 108 days.

(21) Appl. No.: 10/725,387

(22) Filed: Dec. 3, 2003

(65) Prior Publication Data

US 2004/0124128 A1 Jul. 1, 2004

(30) Foreign Application Priority Data

Dec. 25, 2002 (JP) .................................... 2002-375103

(51) Int. Cl.[7] ............................................. B01D 15/08
(52) U.S. Cl. ..................... 210/198.2; 210/101; 210/656
(58) Field of Search .............................. 210/635, 656, 210/659, 198.2, 101; 422/70

(56) References Cited

U.S. PATENT DOCUMENTS

| | | | | |
|---|---|---|---|---|
| 4,837,157 A | * | 6/1989 | Turnell et al. ................. 436/20 |
| 4,872,992 A | * | 10/1989 | Oquendo et al. ............ 210/659 |
| 4,950,397 A | * | 8/1990 | Oquendo et al. ......... 210/198.2 |
| 5,117,109 A | * | 5/1992 | Asakawa et al. ............ 250/288 |
| 5,290,340 A | * | 3/1994 | Gatten et al. .................. 95/46 |
| 6,159,426 A | * | 12/2000 | Palmer et al. ............. 422/68.1 |
| 6,344,172 B1 | * | 2/2002 | Afeyan et al. ................ 422/70 |
| 6,406,632 B1 | * | 6/2002 | Safir et al. .................. 210/656 |
| 6,790,361 B2 | * | 9/2004 | Wheat et al. ................ 210/656 |

* cited by examiner

*Primary Examiner*—Ernest G. Therkorn
(74) *Attorney, Agent, or Firm*—Rader, Fishman & Grauer PLLC

(57) ABSTRACT

In a trap flow path, two diluents are supplied by solvent pumps that can respectively determine the flow rates independently. One of the diluents is allowed to pass through a fraction loop so as to direct a fractioned component(s) held in the fraction loop to a trap column together with a mobile phase. The other diluent is allowed to join with a flow path that has passed through the fraction loop on the downstream side of the fraction loop, and flows to the trap column while diluting the mobile phase from the flow path. In the trap column, the sample component(s) is condensed while being trapped therein.

4 Claims, 4 Drawing Sheets

(1) PRIMARY ANALYSIS (2) CONDENSATION (3) SECONDARY ANALYSIS

LIQUID CHROMATOGRAPH

BACKGROUND OF THE INVENTION

1. Field of the Invention

The present invention relates to a liquid chromatograph such as a high-speed liquid chromatograph, and more particularly, concerns a liquid chromatograph, which has functions for trapping separated component(s) in a trap column for condensing the component(s).

2. Description of the Prior Art

In a conventional two-dimensional high-speed liquid chromatography, an eluent is divided into fractions containing one or more components to be analyzed on the downstream side of a primary analysis column so that the components are adsorbed in a trap column and the like for condensation, and then the components adsorbed in the trap column are desorbed for re-analysis in a secondary analysis.

Upon adsorbing the components into the trap column, in order to increase the adsorbing efficiency of the components to the trap column, a mobile phase, which weakens the solvent strength of the eluent, is sent simultaneously as a diluent. The mixing ratio of the eluent and the diluent, that is, the dilution ratio, is determined by using a resistance tube.

Upon sending a solution for condensation into the trap column, the ratio of a solution used for transporting the eluent fractioned in the primary analysis into the trap column and the diluent effects the adsorbing efficiency greatly; and in the conventional device, since the selection of the dilution rate is made by using a resistance tube, the dilution rate is limited to several values such as 1/3, 1/6 and 1/10, and thereby fails to properly provide various dilution rates.

SUMMARY OF THE INVENTION

The objective of the present invention is to provide a technique in which, upon sending sample components separated and fractioned in the primary analysis together with an eluent to a trap column for condensation, the ratio of a solution used for transporting these to the trap column and a diluent is freely set In the present invention, upon sending a solution for condensation into the trap column, the solution used for transporting the eluent containing sample component(s) separated and fractioned in the primary analysis to the trap column and the diluent are sent by using individual pumps; thus, it becomes possible to freely select the dilution rate.

In other words, the liquid chromatograph of the present invention is provided with a fraction flow path which directs a sample injected from a sample injection port to a primary analysis column with a primary analysis mobile phase for separation and holds separated component(s) of the sample as a fraction together with the mobile phase in a fraction unit; a trap flow path which sends the component(s) and the mobile phase held in the fraction unit to a trap column with a diluent so that the component(s) is trapped for condensation, and an analyzing flow path which directs the component(s) trapped by the trap column to a secondary analysis column with a secondary analysis mobile phase for analysis, wherein a flow path that sends the diluent to the trap column comprises a first diluent flow path that passes through the fraction unit and a second diluent flow path that allows the diluent to join to the first diluent flow path on the downstream of the fraction unit, the first and second diluent flow paths being provided with solvent pumps that determine respective flow rates independently.

In this manner, in the trap flow path, the flow rates of the first and second diluent flow paths can be determined independently so that it becomes possible to freely determine the dilution rate.

In comparison with the conventional method using a resistance tube to determine the dilution rate, it is possible to eliminate the necessity of adjustments of the resistance tube, and consequently leads to lower production costs by reducing the number of processes. Moreover, in the case of the dilution resistance tube, the dilution flow rate tends to vary slightly due to the adsorption of foreign matters on an inner wall of the tube. In contrast, in this arrangement, since the dilution flow rate is determined by the solvent pumps, it is possible to always obtain a stable dilution flow rate.

In a preferable mode, at least one of the solvent pumps installed in the first and second diluent flow paths is jointly used as a solvent pump for a primary analysis mobile phase, on the upstream of which a switching valve which switches the supplies of the primary analysis mobile phase and the diluent is provided. In this manner, the solvent pump is jointly used as the pump for the primary analysis mobile phase and the pump for the diluent so that it has the advantage of reducing the liquid chromatograph device costs.

In another preferable mode, an NMR (Nuclear Magnetic Resonance) substitution flow path for substituting the mobile phase existing at least in the trap column with a heavy-hydrogenated solvent is connected to the trap column. With this arrangement, the component(s) trapped by the trap column is kept in the trapped state without being eluted, and the mobile phase is substituted with the heavy-hydrogenated solvent so that the NMR analysis is available. Additionally, since the capacity to be substituted is limited to the trap column and the slight flow path connected thereto, it is possible to reduce the consumption of the costly heavy-hydrogenated solvent.

DESCRIPTION OF THE PREFERRED EMBODIMENTS

Details of the present invention shall now be described hereinafter with reference to figures.

[Embodiment 1]

Figure 1:
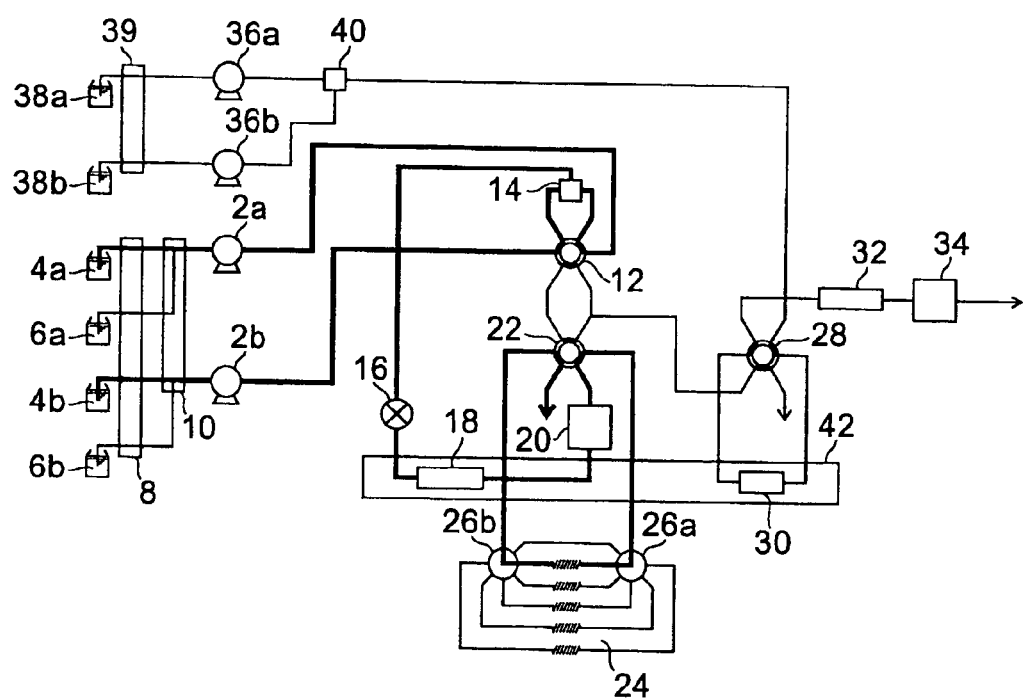
FIG. 1 is a flow-path diagram showing a state in a primary analyzing process in accordance with a first embodiment.

FIG. 1 shows the first embodiment.

Two solvent pumps 2a and 2b, which can independently determine flow rates of a primary analysis mobile phase and a diluent to be supplied, are installed. Flow paths of an organic solvent 4a serving as the primary analysis mobile phase and a diluent 6a are connected to the solvent pump 2a. The organic solvent 4a and the diluent 6a are connected to the solvent pump 2a through an online degasser 8 that prevents inclusion of gas and a switching valve 10. The switching valve 10 makes a switch to either the flow path for the organic solvent 4a or the flow path for the diluent 6a so as to be connected. In the same manner, flow paths of water 4b serving as a primary analysis mobile phase and a diluent 6b are connected to the other solvent pump 2b. The water 4b and the diluent 6b are also connected to the solvent pump 2b through the online degasser 8 and the switching valve 10 so that the switching valve 10 makes a switch to either the flow path for water 4b and the diluent 6b so as to be connected.

The diluents 6a and 6b are the same solution, and such a solvent as to increase the adsorbing efficiency to a trap column is selected and used in compliance with the mobile phases 4a and 4b.

The downstream flow paths of the solvent pumps 2a and 2b are connected to a mixer 14 which mixes the solutions of the two flow paths through a switching valve 12, and a flow path for the solution mixed in the mixer 14 is connected to a primary analysis column 18 through an auto-sampler 16 that forms a sample introducing port.

The downstream flow path of the analysis column 18 is connected to a UV (ultraviolet ray) detector 20 so that components separated by the analysis column 18 are detected by the detector 20.

The downstream flow path of the detector 20 is connected to a fraction loop 24 through a switching valve 22. This fraction loop 24 is provided with a plurality of flow paths that are aligned in parallel with one another between two distributing valves 26a and 26b, and fractioned components and mobile phases can be held in the respective paths. A flow path directed to a drain is also connected to the switching valve 22.

Two flow paths are connected between the valves 12 and 22, and one flow path is branched and connected to a switching valve 28. A trap column 30 is connected to the switching valve 28, to which a secondary analysis column 32 is further connected. A UV detector 34 is connected to a downstream flow path of the analysis column 32.

Two solvent pumps 36a and 36b are installed so as to supply secondary analysis mobile phases. Flow paths used for an organic solvent 38a and water 38b that are secondary analysis mobile phases are connected respectively to the solvent pumps 36a and 36b through an on-line degasser 39. Down stream flow paths of the solvent pumps 36a and 36b are connected to the switching valve 28 through a mixer 40 which mixes the solutions of the two flow paths.

Reference numeral 42 denotes a column oven which maintains the columns 18 and 30 at a fixed temperature.

With respect to the analysis columns 18 and 32, various columns such as a forward-phase column, a reverse-phase column, an ion exchange column, an affinity chromato-column and a GPC (gel permeation chromatography) column, are selected and used in compliance with the components to be separated and analyzed. With respect to the trap column 30, the same types of columns as the analysis columns 18 and 32 having shorter lengths can be used.

The operations of this embodiment shall now be described.

(Primary Analysis)

FIG. 1 shows primary analyzing and fractioning processes. Portions of flow paths indicated by thick lines represent flow paths that are used for the operations of these processes. The same is true for the explanations of the ensuing drawings.

The solvent pumps 2a and 2b send the solutions with the mobile phases 4a and 4b being selected by the switching valve 10. The mobile phases are sent through the switching valve 12 to the mixer 14 in which these are mixed, and then allowed to flow through the analysis column 18 via the auto-sampler 16. The sample injected from the auto-sampler 16 is separated in the analysis column 18 for elution, and detected by the detector 20. When peak detection is carried out by the detector 20, the distributing valves 26a and 26b are operated in response to the resulting signal so that a sample component(s) detected is held together with the mobile phase as a fraction in any portion of the fraction loop 24. That is, each time when a peak is detected by the detector 20, the distributing valves 26a and 26b are switched so that the sample component(s) detected and the mobile phase are held as a fraction in each portion of the fraction loop 24.

A portion of the mobile phase that flows out of the analysis column 18 without being held by the fraction loop 24 is discharged to the drain.

During this process, the secondary analysis mobile phases 38a and 38b from which bubbles have been removed by the on-line degasser 39 are still supplied through the solvent pumps 36a and 36b and mixed by the mixer 40, through which the mixed mobile phase is sent to the secondary analysis column 32 for conditioning thereof.

(Condensation)

Figure 2:
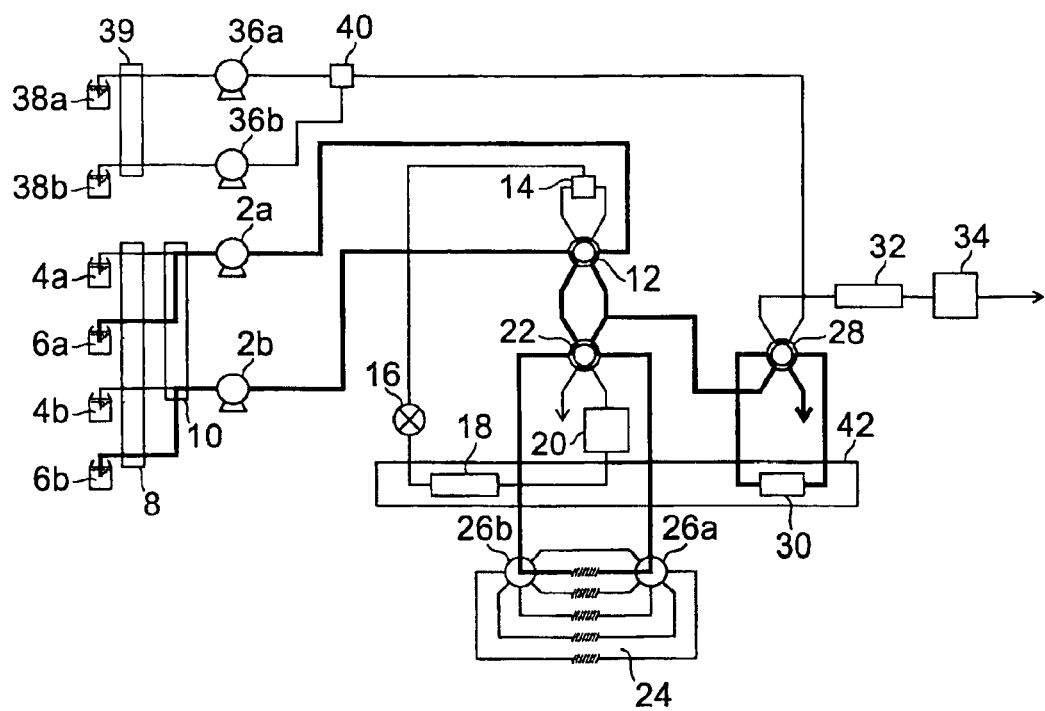
FIG. 2 is a flow-path diagram showing a state in a condensing process in the same embodiment.

Next, FIG. 2 shows a condensation process in which the fractioned component(s) held by the fraction loop 24 is trapped by the trap column 30 for condensation.

The switching valve 10 is switched so that the diluents 6a and 6b are supplied by the solvent pumps 2a and 2b. The diluent supplied by the solvent pump 2b is allowed to pass through a predetermined fraction loop 24 through the switching valves 12 and 22 and the delivery valve 26b so that the fractioned component and the mobile phase held by the predetermined fraction loop 24 are directed to the trap column 30 through the delivery valve 26a and the switching valves 22 and 28. At this time, the diluent 6a is supplied through the pump 2a and the switching valve 12, and joined to the flow path that runs through the fraction loop 24, and directed to the trap column 30 while diluting the mobile phase supplied from the flow path. In the trap column 30, the sample component(s) is condensed while being trapped. The mobile phase and the diluent that have passed through the trap column 30 are discharged to the drain through the switching valve 28.

During these processes, the mobile phase is still allowed to flow through the secondary analysis column 32 for conditioning thereof.

(Secondary Analysis)

Figure 3:
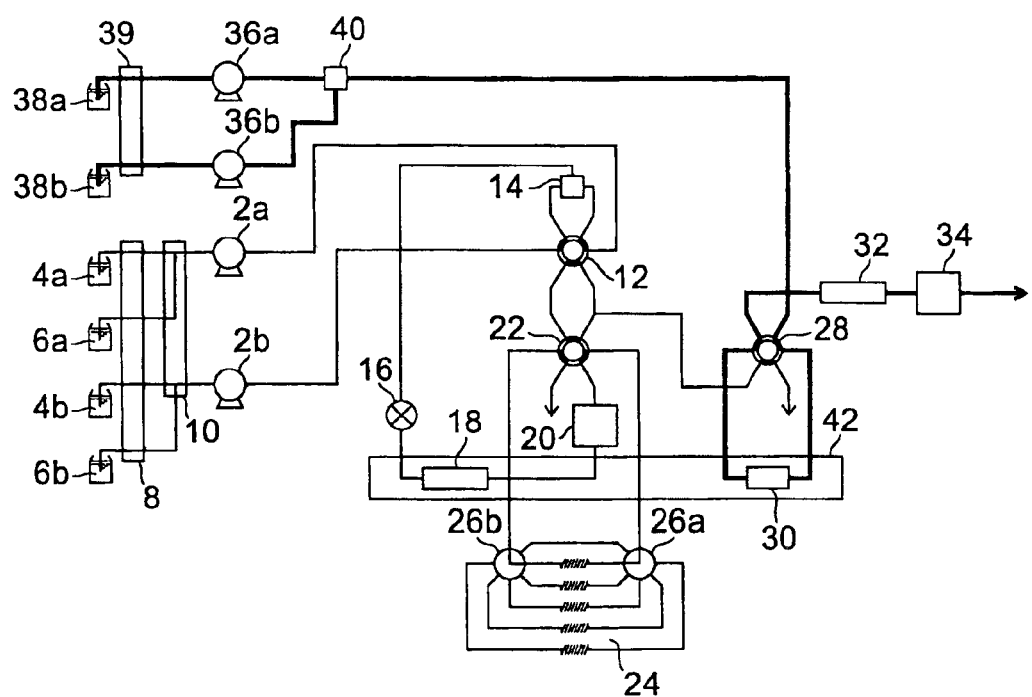
FIG. 3 is a flow-path diagram showing a state in a secondary analyzing process in the same embodiment.

FIG. 3 shows processes in the secondary analysis.

The secondary analysis mobile phases 38a and 38b from which bubbles have been removed by the on-line degasser 39 are respectively supplied through the solvent pumps 36a and 36b, and mixed by the mixer 40, and further sent The mixed mobile phase is allowed to reach the trap column 30 through the switching valve 28, and the sample component(s) trapped by the trap column 30 is eluted and directed to the secondary analysis column 32 through the switching valve 28. The sample component(s) directed to the analysis column 32 is further separated by the analysis column 32 for elution, and then detected by the detector 34.

The objective of the high-speed liquid chromatograph is achieved by the secondary analysis. Furthermore, a mass spectrometer (MS) for use in qualitative analysis may be connected to the downstream side of the detector 34. In this case, the eluent that has passed through the detector 34 is directed to the mass spectrometer through an appropriate interface so that the sample component detected by the detector 34 is subjected to a qualitative analysis.

[Embodiment 2]

Figure 4:
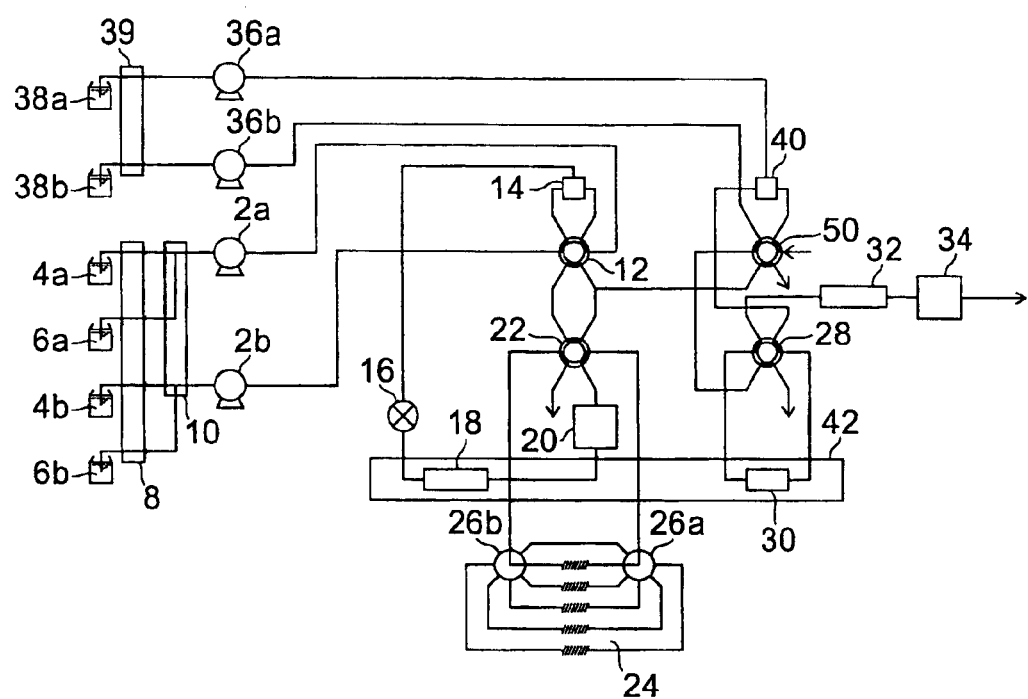
FIG. 4 is a flow-path diagram showing a second embodiment.

FIG. 4 shows the second embodiment in which a function for carrying out a substituting process by using a heavy-hydrogenated solvent so as to conduct an NMR analysis is added to the first embodiment.

As the secondary analysis mobile phase in the embodiment shown in FIG. 1, a heavy-hydrogenated organic solvent is used as the secondary analysis organic solvent 38a, and a heavy water is used as the water 38b. Further, a switching valve 50 is inserted between the flow path from the switching valves 12, 22 as well as the mixer 40 and the switching valve 28 so that the substituting process can be carried out by using the heavy water through the switching valve 50.

In this embodiment, after the sample component(s) has been trapped in the trap column 30, prior to directing the component(s) to the analysis column 32, the heavy water 38b is supplied by the solvent pump 36b, and discharged from the switching valve 28 to the drain through the switching valve 50 and the trap column 30 without passing through the mixer 40. Due to this, the inside of the trap column 30 and the flow paths between the switching valve 28 and the trap column 30 are replaced by heavy water. Consequently, the component(s) trapped by the trap column 30 is kept in the trapped state without being eluted.

Next, the switching valves 50 and 28 are switched so that the heavy-hydrogenated organic solvent 38a is supplied by the solvent pump 36a, with the heavy water 38b being supplied by the solvent pump 36b, so that a gradient analysis is carried out In this case, the heavy-hydrogenated organic solvent 38a is sent to the mixer 40, and the heavy water 38b is sent to the mixer 40 through the switching valve 50 so that the heavy-hydrogenated organic solvent 38a and the heavy water 38b are mixed in the mixer 40 to form a gradient-analysis mobile phase, and the mobile phase is allowed to reach the trap column 30 through the switching valve 28 so that the sample component(s) trapped by the trap column 30 is eluted and directed to the secondary analysis column 32 through the switching valve 28. The sample component(s) directed to the analysis column 32 is further separated by the analysis column 32 for elution, and then detected by the detector 34.

In this embodiment, the mobile phase is substituted with the heavy-hydrogenated solvent so that an NMR analysis is available.

What is claimed is:

1. A liquid chromatograph comprising:

a fraction flow path which directs a sample injected from a sample injection port to a primary analysis column with a primary analysis mobile phase for separation, and holds separated component(s) of the sample as a fraction together with the mobile phase in a fraction unit;

a trap flow path which sends the component(s) and the mobile phase held in the fraction unit to a trap column with a diluent so that the component is trapped for condensation, wherein a flow path that sends the diluent to the trap column comprises a first diluent flow path that passes through the fraction unit and a second diluent flow path that allows the diluent to join with the first diluent flow path on the downstream of the fraction unit, the first and second diluent flow paths being provided with solvent pumps that determine respective flow rates independently; and an analyzing flow path which directs the component(s) trapped by the trap column to a secondary analysis column with a secondary analysis mobile phase for analysis.

2. The liquid chromatograph according to claim 1, wherein at least one of the solvent pumps installed in the first and second diluent flow paths is jointly used as a solvent pump for a primary analysis mobile phase, on the upstream of which a switching valve which switches the supplies of the primary analysis mobile phase and the diluent is provided.

3. The liquid chromatograph according to claim 1, wherein the fraction unit is provided with a fraction loop which comprises a plurality of flow paths aligned in parallel with one another that are selectable by using distributing valves.

4. The liquid chromatograph according to claim 1, wherein an NMR substitution flow path for substituting the mobile phase existing at least in the trap column with a heavy-hydrogenated solvent is connected to the trap column.

* * * * *